US00PP08798P

United States Patent [19]

Richards

[11] Patent Number: Plant 8,798

[45] Date of Patent: Jun. 21, 1994

[54] **ORCHIDACEAE *CATTLEYA WALKERIANA* 'KENNY'**

[76] Inventor: Kerry A. Richards, 6900 SW. 102nd Ave., Miami, Fla. 33173

[21] Appl. No.: 86,141

[22] Filed: Jul. 2, 1993

[51] Int. Cl.[5] ..... A01H 5/00

[52] U.S. Cl. ..... Plt./87.3

[58] Field of Search ..... Plt. 87.4

*Primary Examiner*—James R. Feyrer

[57] ABSTRACT

A new and distinct variety of Orchidaceae plant and more particularly of the genus Cattleya; species *walkeriana;* variety semi-alba, which is outstanding and distinct from other Orchidaceae because of its outstanding plant vigor and free flowering ability. The new variety is also distinctive from its siblings in the grex population by its superior flowers, which combine a rare coloring, massive size and strong carriage of multiple flowers on a single stem. The coloring is an exceptionally glistening white with heavy substance with the lip also white, with apple green coloration at the base of the column, pale yellow in the center of the lip and a fuchsia blush at the lower edge.

The flowers are of exceptional substance, with more rigid petals than siblings of the grex. The flowers are perfectly placed on the stem, which is superior to its species in strength. The flowers are produced more freely and last longer than other Orchidaceae of this species.

2 Drawing Sheets

The present invention comprises a new and distinct cultivar of *Cattleya walkeriana* Var. semi-alba.

The Orchidaceae plant of this application was discovered by the undersigned, as an outstanding member from a large sibling population of *Cattleya walkeriana* albas and semi-albas.

In February of 1979, the large sibling population, aforementioned, was initiated at Limrick® orchid nursery in South Miami, Fla., by the crossing of Cattleya walkeriana 'Pendentive' (pod parent) an 'alba' form, with Cattleya walkeriana 'Hunabu®' a semi-alba of good quality.

The resulting seeds were sown 'in vitro' and grown to maturity at the aforesaid nursery.

On Jan. 8, 1985, the new variety appeared as a single outstanding cultivar among the population of siblings, all cultivated and blooming at the aforesaid nursery. The plant of the new variety was immediately recognized by the applicant, as far superior in its growth and flowering habit to all the members of the large population group of siblings that resulted from the above crossing. On Jan. 11, 1989, this superior new variety was awarded an 'Award of Merit' (87 points) by the American Orchid Society. Also at this time, after the new variety had been observed for a period of time; its other features of superior growth, freedom of bloom with multiple very well shaped flowers of great substance and plant vigor were also noted and the clone was given the varietal name 'Kenny' to identify it from all others.

ASEXUAL REPRODUCTION

After its discovery in 1985, an immature front lead of the original 'Kenny' was placed in the laboratories of H & R Nurseries, Inc., 41-240 Hihimanu Street, Waimanalo, Hi., and a large number of plants of the new variety were asexually produced by the meristem tissue culture process, under contract, with the code number "KR-112". Portions of the meristematic cells, capable of later differentiation, were taken from the plant and developed under extreme aseptic, in-vitro conditions, into new plants. This has been an on going delicate process to cultivate this new and distinct variety of Orchidaceae.

The population of plants thus propagated asexually from this cultivar carries this exact code "KR-112".

The propagules asexually reproduced from the original plant, have been true to the original in both plant, flower and other superior characteristics that identified it at discovery. Of the cross section of the new variety of asexually propagated plants that have flowered, there have been no signs of mutations and are all identical to the original 'Kenny'. All plants of this new variety have continued to be readily distinguishable from both parent plants and all other siblings; in plant growth by the addition of front leads, more usually two than the one that the parent and sibling plants exhibit; in flower quality by the heavier substance, full round shape with multiple flowers than that of its parent plants or siblings of the cross.

DESCRIPTION OF THE PHOTOGRAPHS

The photographs show:

1. A view of the entire plant to reveal the growth habit, general characteristics with its flowers, which is typical of this new variety; (left and right.)

2. A close up view of its flowers, to show their full round form, large size and glistening texture that is typical of this new variety.

DESCRIPTION OF THE PLANT

The plant and its flowers are illustrated in the color photographs accompanying this specification. In some respects the plant is typical of a *Cattleya walkeriana.* However, because of the distinct markings and coloration of this particular cultivar, combined with the great frequency and freedom of bloom, it is superior and unique.

In short, one or two leaves per pseudobulb are erectly carried of elliptic to oblong shape with an obtuse apex and are of fairly uniform size in mature specimens. The average leaf is ten to fifteen centimeters long and six to eight centimeters wide and slightly involute on a mature specimen, this does not include the pseudobulb.

The plant, which is of dwarf stature, typical of the species, attains a growth at maturity of fifteen to twenty five centimeters. The plant develops a structure of superior and unusual vigor with resiliency in all its parts. The plant is short rhizomed, compact, with many flowering leads. The growth, in addition to being compact, is naturally erect, without need to support the leaves or flower stems. The strong flower sprays are borne from the axils of the growth and are of superior strength and well carried on strong stems.

Its flowering habit is dependable as the flowers develop from small bracts throughout the year in the south Florida climate. A unique free flowering plant of special value.

The plant's resistance to disease and its extreme vigor, single out this cultivar as superior to its sibling population.

This new cultivar's population have been pathogen free, during development and the meristeming process, including the mature plants. The plant growth habit and ease of meristeming, with uniform cytology and no aneuploidial characteristics are indicative of a more than di-ploid chromosome compliment, but the ploidy of this plant has not been firmly ascertained.

DESCRIPTION OF THE FLOWER

The color values presented in the following are taken by reference to "The Royal Horticultural Society Colour Chart" prepared by The Royal Horticultural Society, London. Color descriptions of ordinary meaning are presented where appropriate.

The non-fragrant flowers produced by this plant are unusually large and showy for the size of the plant and of the species, and of unusually attractive character and value within "Cattleya walkeriana". The shape of the flowers produced is of extraordinary rounded shape and uncommonly full for this market class; with the sepals, petals and lip being of heavier than normal in substance. The heavy substance of these flower parts allows the flowers to retain a delicate, waxy texture and almost synthetic, pleasing appearance which glistens and is nearly pure white in normal light. Individual flowers are so spaced along the flower stem as to attractively allow them to overlap at the sepals and petals of adjacent individual flowers; with flowers being oriented at an angle approaching ninety degrees to the axis of the nearly vertical, strong flower stem. The size, shape and arrangement of the parts of the flowers of this plant appear uncommonly attractive and perfectly balanced.

The predominant base or ground color of all of the flower parts is white, near RHS 155D. Sepals and petals are nearly pure white. Sepals are substantially elliptic with a cuspidate apex. The small cuspidate apex presents an excurrent tip of green near RHS 134B which blends subtily into the white of the sepals in a distance of about the length of the tip itself. Sepal margins are entire and strikingly contrasting when compared to those of the more billowy petals, which are minutely undulate. Sepal length is about the same as that of the petals; sepal width is about half that of the petals. Petal is deltoid in shape, each having a blunt apex. Petal margins are entire but appear indented due to slight to moderate ruffles and crinkles, or minute undulations, which occur along marginal petal portions, allowing the petals to stand out distinctly over sepals, of the same pleasing color, due to shading. Petals and side lobes of the labellum are imbricated over basal sepal blade portions. The side labellum lobes flare outwardly to overlap and conceal the basal portions of the petals. Ribbing and veining of both sepals and petals is essentially inconspicuous.

The column is presented in the form of a proboscis which is frramed by the outwardly flaring upper lobes of the labellum. The upper attachment point of the column defines a line between the basal attachments of the petals, and is slightly shaded with faint hues of green, near RHS 145C, which diminish progressively with greater distance from the brow-like attachment line. The bridge of the column is moderately mounded between opposite flaring laterally extending portions.

The lip is distinctly three-lobed. The mid lobe is bipartite and substantially emarginate, forming a sinus at the apex. The side lobes seperated from the mid lobe by clefts. The margins of the lip are very finely minutely crenualated on the side lobes and finely indented on the mid lobe. The surface aspect of the mid lobe is crinkled while the lobe surface is relatively smooth to finely but irregularly crimped. The central, throat portion of the lip presents a faint overcolor of pale yellow shades near RHS 4D to golden over the white color, which fade gradually toward marginal portions of the mid lobe. Just within the front edge of the mid lobe, a bright splotch of fuchsia, near RHS 80C, attractively highlights the lip. The markings of the splotch are most intensive in the veining and appear as brush strokes symmetrical to each side, fused at the center of the lip. The basal parts of the wing-like lobes appear to attempt to clasp the basal, attachment portion of the column but are seperated by the width of the column.

The flowers of the new variety are larger and heavier in substance than the average cultivar in this species. The flowers average 4.3 centimeters in petal width, with a petal length of 4.9 centimeters average. The total span of the flower averages 8.8 centimeters. The new variety can carry as many as three to six flowers on each spray with four flowers being the norm, on a mature well grown plant. Additionally because of the compactness of the plant and its free flowering ability, a single plant can have from two to five sprays of flowers in a single growth cycle. Also the petals overlap the sepals and lip, all in the same plane, which gives the flower its round form. As the flower opens, it does so without twisting or curving back, which makes for its symmetrical balance and extreme round shape, that is sought after by hybridizers and presents a level of excellence to 37 Cattleya" growers, showers and the buyers in the industry.

What is unique and distinct about this cultivar, is the uniformity of flower quality and color form; one blooming to the next, regardless of culture conditions or temperature, with blooms lasting ten days on the average. The plant has been found to be fertile when cross pollinated both as a pod parent and provider of fertile pollen.

The above described growth and flowering characteristics of the new variety, make it of exceptional value in the commercial orchid plant sales market. The plant vigor, free blooming habit and color are characteristics which set this particular cultivar above, not only siblings in this grex, but other gregi in this entire line of breeding. By introducing this cultivar into commerce we expect it to perform as an exceptional new variety of Orchidaceae adaptable to most orchid growing environments.

Due to the exceptional overall characteristics of this plant and particularly in terms of attractive flower character and appearance, and plant productivity, it is anticipated that this plant will be a valuable addition to commerce. Moreover, due to its clear and distinct superiority in cultural ease, floral characteristics and repeat blooming, it is expected that this plant will contribute to future development within this botanical market class of orchids as a superior germplasm resource.

What is claimed is:

1. A new and distinct plant in the Orchidaceae family in the genus Cattleya, discovered as a superior selection within the grex *Cattleya walkeriana* var. semi-alba, substantially as described and illustrated, namely 'Kenny', characterized by a combination of clearness of coloring, superior flower substance and glistening texture, size and shape, further characterized by the exceptional vigor, freedom to bloom and dramatic flower qualities.

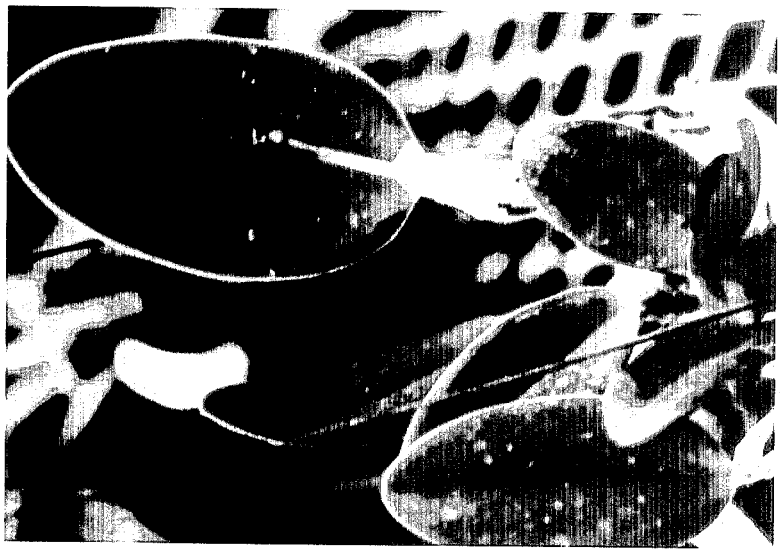
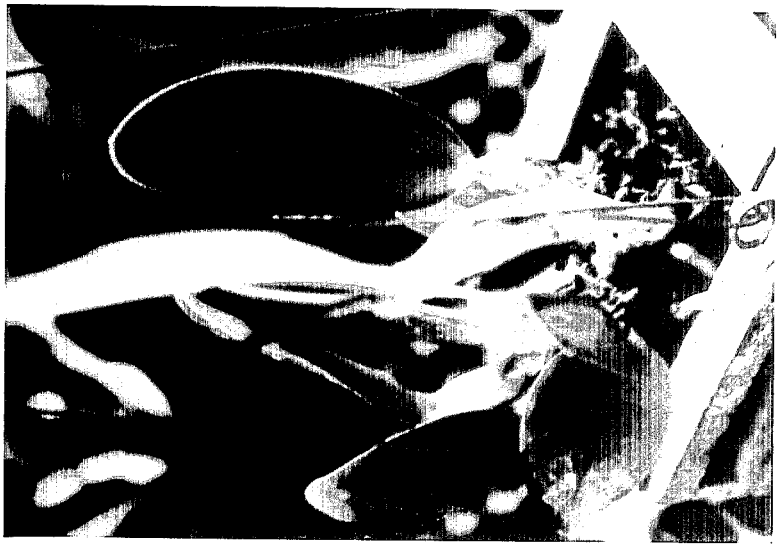

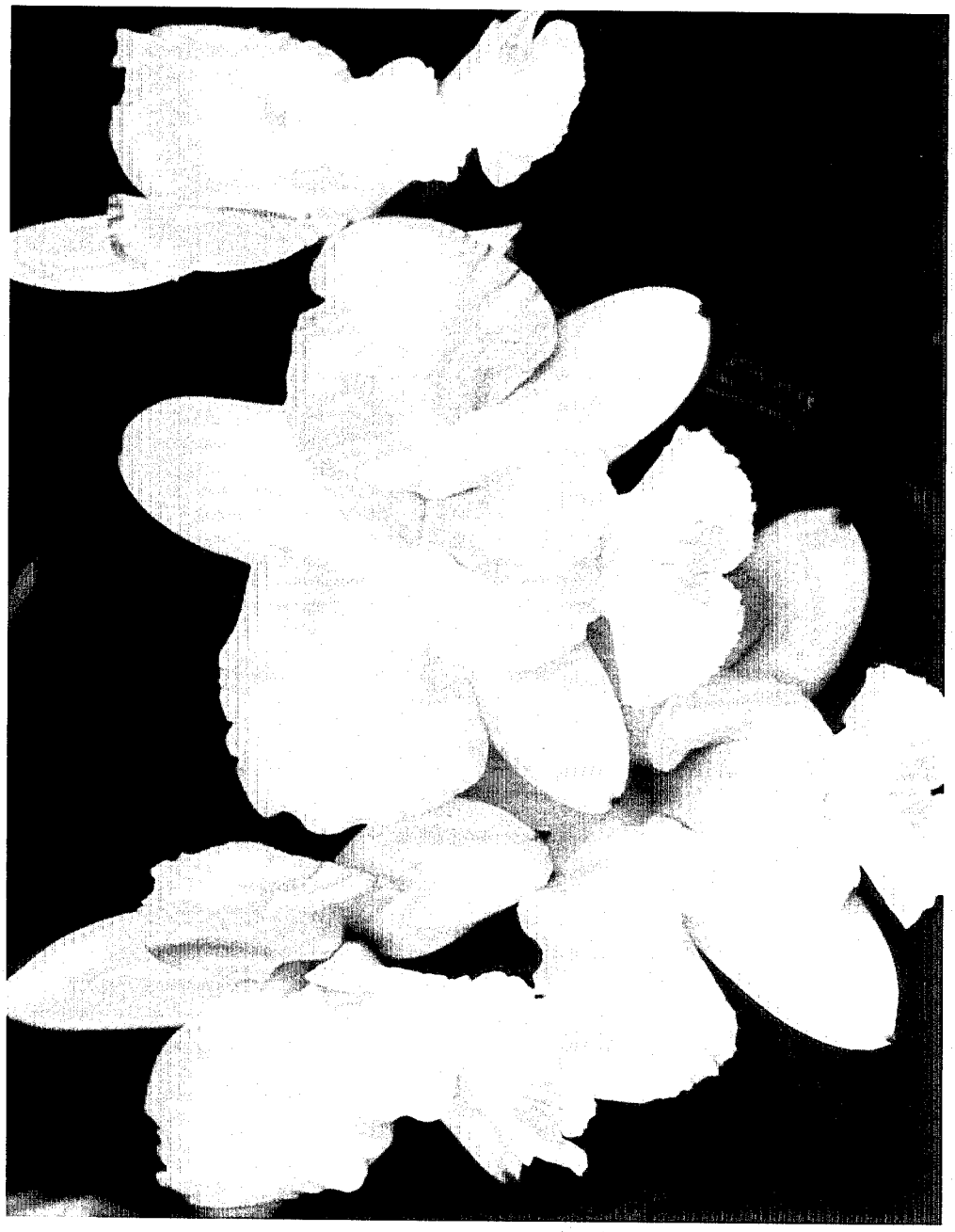

* * * * *